United States Patent
Okumura et al.

(10) Patent No.: US 11,559,190 B2
(45) Date of Patent: Jan. 24, 2023

(54) STEERABLE MEDICAL DEVICE AND METHOD

(71) Applicant: Canon U.S.A. Inc., Melville, NY (US)

(72) Inventors: Ichiro Okumura, Abiko (JP); Takahisa Kato, Brookline, MA (US)

(73) Assignee: Canon U.S.A., Inc., Melville, NY (US)

(*) Notice: Subject to any disclaimer, the term of this patent is extended or adjusted under 35 U.S.C. 154(b) by 428 days.

(21) Appl. No.: 16/604,914

(22) PCT Filed: Apr. 27, 2018

(86) PCT No.: PCT/US2018/029996
§ 371 (c)(1),
(2) Date: Oct. 11, 2019

(87) PCT Pub. No.: WO2018/204202
PCT Pub. Date: Nov. 8, 2018

(65) Prior Publication Data
US 2020/0383670 A1 Dec. 10, 2020

Related U.S. Application Data

(60) Provisional application No. 62/500,723, filed on May 3, 2017.

(51) Int. Cl.
*A61B 17/00* (2006.01)
*A61B 1/00* (2006.01)
(Continued)

(52) U.S. Cl.
CPC .............. *A61B 1/0052* (2013.01); *A61B 1/06* (2013.01); *A61B 17/00234* (2013.01); *A61B 1/00154* (2013.01); *A61B 10/04* (2013.01); *A61B 17/320016* (2013.01); *A61B 2017/003* (2013.01); *A61B 2017/00305* (2013.01);
(Continued)

(58) Field of Classification Search
CPC ......... A61B 1/00154; A61B 1/06; A61B 1/04; A61B 1/0057; A61B 1/0052; A61B 2017/00867; A61B 2017/00336; A61B 2017/00323; A61B 2017/00314; A61B 2017/00305; A61B 2017/003; A61B 17/320016; A61B 17/00234; A61M 25/0062
See application file for complete search history.

(56) References Cited

U.S. PATENT DOCUMENTS

| | | | | |
|---|---|---|---|---|
| 3,162,214 A | * | 12/1964 | Bazinet, Jr. ........ | A61B 1/0055 138/120 |
| 5,531,664 A | * | 7/1996 | Adachi ............... | A61B 1/0058 600/149 |
| 5,938,587 A | | 8/1999 | Taylor et al. | |

(Continued)

FOREIGN PATENT DOCUMENTS

| | | |
|---|---|---|
| CN | 103200896 A | 7/2013 |
| JP | 2007503285 A | 2/2007 |

(Continued)

*Primary Examiner* — Jocelin C Tanner
(74) *Attorney, Agent, or Firm* — Canon U.S.A., Inc. IP Division

(57) ABSTRACT

An apparatus, method, and system for a steerable medical device, configured to be used in conjunction with guide tools and devices in medical procedures, including endoscopes, cameras, cutting tools and catheters.

20 Claims, 7 Drawing Sheets

(51) Int. Cl.
*A61B 1/06* (2006.01)
*A61B 10/04* (2006.01)
*A61B 17/32* (2006.01)
*A61M 25/06* (2006.01)
*A61B 1/005* (2006.01)

(52) U.S. Cl.
CPC .............. *A61B 2017/00867* (2013.01); *A61M 25/0662* (2013.01)

(56) References Cited

U.S. PATENT DOCUMENTS

| | | | |
|---|---|---|---|
| 8,753,263 B2 | 6/2014 | Arai | |
| 9,039,607 B2 | 5/2015 | Buehs | |
| 2002/0017515 A1* | 2/2002 | Obata | A61B 1/0055 219/137 R |
| 2007/0232858 A1* | 10/2007 | Macnamara | A61B 1/0051 600/149 |
| 2009/0143647 A1* | 6/2009 | Banju | A61B 1/0057 600/149 |
| 2009/0192357 A1 | 7/2009 | Torii | |
| 2009/0209820 A1* | 8/2009 | Tanaka | A61B 1/0052 600/149 |
| 2009/0323146 A1 | 12/2009 | Cui | |
| 2010/0280449 A1* | 11/2010 | Alvarez | A61M 25/0138 606/1 |
| 2011/0021875 A1 | 1/2011 | Macnamara et al. | |
| 2012/0123441 A1 | 5/2012 | Au et al. | |
| 2013/0150673 A1 | 6/2013 | Kakehashi | |
| 2015/0011830 A1 | 1/2015 | Hunter et al. | |
| 2015/0366572 A1 | 12/2015 | Sholev | |
| 2015/0374205 A1 | 12/2015 | Kato | |
| 2016/0038003 A1* | 2/2016 | Imai | A61B 1/0052 600/149 |
| 2017/0150871 A1* | 6/2017 | Arai | A61B 1/05 |

FOREIGN PATENT DOCUMENTS

| | | |
|---|---|---|
| JP | 2009172028 A | 8/2009 |
| JP | 2014504897 A | 2/2014 |
| JP | 2017505199 A | 2/2017 |

* cited by examiner

STEERABLE MEDICAL DEVICE AND METHOD

CROSS REFERENCE TO RELATED PATENT APPLICATIONS

This application claims priority from U.S. Provisional Patent Application No. 62/500,723 filed on May 3, 2017, in the United States Patent and Trademark Office, the disclosure of which is incorporated herein in its entirety by reference.

FIELD OF THE DISCLOSURE

The present disclosure relates generally to apparatus and methods for medical application and, more particularly to a steerable medical device applicable to guide tools and devices in medical procedures, including endoscopes, cameras, and catheters.

BACKGROUND OF THE DISCLOSURE

Flexible medical instruments such as endoscopic surgical devices and catheters are broadly used in surgical and probative settings, and continue to gain acceptance in the medical field. The medical devices generally include a flexible tube commonly referred to as a sleeve or sheath, with one or more tool channels extending along (typically inside) the sheath to allow access to end effectors located at a distal end of the sheath.

The device is projected to provide flexible access with at least one curve or more to an intended lesion in a confined space, while retaining torsional and longitudinal rigidity through narrow pathways. Physicians actuate the end effectors located at the distal end of the sheath by maneuvering a proximal end of the device from outside of the patient. Therefore, actuation of the sheath from the distal end plays a key role in ensuring flexible access to the end effectors, while achieving physicians' controllability for the devices, thus aiding the physician in probing and/or operating on the patient.

By way of example, U.S. Pat. No. 8,365,633 ("633 patent"), provides a push-pull actuation surgical device for surgery, having a multi-backbone sheath. Among the multiple backbones, one primary backbone is centrally located and is attached to a base disk and an end disk. The secondary backbones are attached to the end disk and are equidistant from each other. To generate bending moments, the secondary backbones are pushed and pulled against the base disk. The secondary backbones are connected to actuation units that include linear sliders and motors and are actuated by these motors.

However, the existing art suffers from a multitude of drawbacks which limit and hinder the use of flexible medical devices. For instance, the secondary backbones in '633 patent is limited in size reduction, as the secondary backbones need to travel through free space between the sheath and the actuator. Since this free-standing length causes buckling of the second backbones in pushing operation, the diameter of the secondary backbones are limited to maintain enough stiffness to avoid buckling. Accordingly, buckling of the secondary backbones stagnates miniaturization of the sheath.

Furthermore, because of the secondary backbones in the '633 patent, the device cannot extend for a long distance in free-space, hence, the actuators need to be located close to the proximal end of the secondary backbones. This limitation of the actuators causes difficult integration of multiple actuators, and substantially limits the range and usability of the '633 patent device. Additionally, the circular pitch of the secondary backbones cannot be reduced because of the mechanical interference of the adjacent actuators. Therefore, the miniaturization of the sheath is further limited.

Accordingly, it is particularly beneficial to disclose a steerable medical device boasting a reduced overall diameter, while capable of controlled manipulation of the device in three axes.

SUMMARY

Thus, to address such exemplary needs in the industry, the presently disclosed apparatus, systems, and methods teach a medical apparatus utilized in non-evasive surgical procedures, comprising a bendable body for insertion into the patient, with at least a first driving wire configured in the bendable body, and an expansion unit comprising a first break-out wire attached to the first driving wire and a contracting guide that is movable against the first driving wire, wherein the first break-out wire is connected to an actuator configured to maneuver the bendable body.

In various embodiments, the first driving wire extends to a distal end of the bendable body and is offset from a center line of the bendable body to allow for a hollow passageway through the center of the bendable body, the hollow passageway allowing for conventional surgical tools and instruments to pass through the center of the bendable body, such that the tools and instruments can reach an internal element of a patient.

In other embodiments of the subject disclosure, the medical apparatus may further comprising a second, third and/or additional driving wires configured in the bendable body, as well as corresponding second, third and/or additional break-out wires attached to the corresponding driving wire, wherein the second, third and/or additional break-out wires are connected to the actuator, allowing the actuator to manipulate the bendable body.

In other embodiment, the second, third and/or additional driving wires may at least partially extend into the bendable body, wherein the second, third and/or additional driving wires are offset from a center line of the bendable body, thus preserving or promoting the hollow passageway through the center of the bendable body.

In various embodiment of the subject disclosure, the actuator is configured to independently retract and advance the first, second, third and/or additional driving wires via manipulation of the corresponding first, second, third and/or additional break-out wires.

In other embodiments, the subject medical apparatus comprises at least one contracting guide parallel to first driving wire for at least a portion of the first driving wire, whereas the contracting guide may be situated to surround the first driving wire, and may further be configured to contact the first driving wire.

In some embodiments, the contracting guide may be at least one primary coil spring parallel to first driving wire, whereas the spring may be situated to surround the first driving wire, and may further be configured to contact the first driving wire.

Additional springs may be utilized to surround additional driving wires.

In various embodiments, a secondary coil spring may be incorporated in the contracting guide in combination with the primary coil spring to surround the first driving wire, such that the primary coil spring and secondary coil spring work in conjunction with one another upon the first driving wire. In various embodiments, the primary coil spring may be configured in spiral direction different than that of the secondary coil spring.

In various embodiments, the break-out unit may be configured such that the diameter of the first break-out wire is greater than a diameter of the first driving wire. Furthermore, second, third and/or additional break-out wires may have a diameter greater than a diameter of the corresponding second, third and/or additional driving wires.

In various embodiments, the break-out unit for housing the at least one break-out wire may comprise one or more guide tube(s), wherein the guide tube(s) may be of similar or different diameter. The guide tube(s) can be configured to guide the break-out wire, such as guiding the break-out wire, such as guiding the break-out wire along the path define by the guide tube.

In further embodiment of the subject apparatus, the bendable body may comprise a backbone, and at least two bending sections which may be configured on the backbone, wherein the at least two bending sections are aligned parallel to one another and have a distance between them, thus creating a space for bending the at least two bending sections. The bending sections each further comprise at least two guide fissures configured to at least accept the first driving wire or the second driving wire.

In various embodiments, the break-out unit may be configured to increase the offset distance of the driving wire proximal to the actuator of the apparatus. In various embodiments, the actuator comprises an actuation handle in communication with the first break-out wire, such that manipulation of the actuation handle corresponds to a bending of the bendable body. In the advent of additional break-out wires and corresponding driving wires, additional actuation handles designated for and attached to each break-out wire, may be utilized for manipulating bendable body.

In other contemplated embodiment, the break-out unit is configured to be detachable from the actuator unit. Furthermore, the bendable body may be configured to be detachable from the break-out unit.

These and other objects, features, and advantages of the present disclosure will become apparent upon reading the following detailed description of exemplary embodiments of the present disclosure, when taken in conjunction with the appended drawings, and provided paragraphs.

BRIEF DESCRIPTION OF THE DRAWINGS

Further objects, features and advantages of the present invention will become apparent from the following detailed description when taken in conjunction with the accompanying figures showing illustrative embodiments of the present invention.

Figure 1:
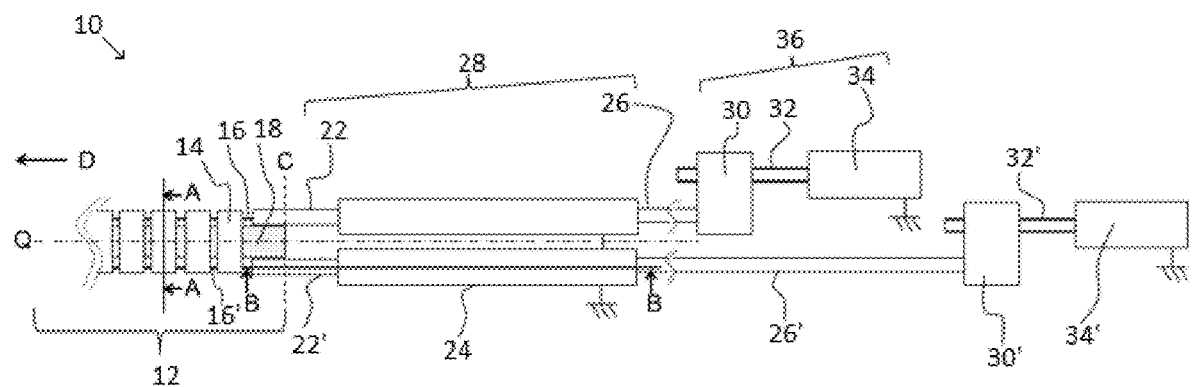
FIG. 1 depicts a side perspective view of a steerable medical device, according to one or more embodiments of the present subject matter.

Throughout the Figures, the same reference numerals and characters, unless otherwise stated, are used to denote like features, elements, components or portions of the illustrated embodiments. In addition, reference numeral(s) including by the designation "'" (e.g. 12' or 24') signify secondary elements and/or references of the same nature and/or kind. Moreover, while the subject disclosure will now be described in detail with reference to the Figures, it is done so in connection with the illustrative embodiments. It is intended that changes and modifications can be made to the described embodiments without departing from the true scope and spirit of the subject disclosure as defined by the appended paragraphs.

DETAILED DESCRIPTION OF THE DISCLOSURE

The present disclosure details a medical device capable of being steered for guidance through passages. More specifically, the subject medical device contains a cavity for accepting medical tools and devices including endoscopes, cameras, and catheters, and the ability to guide or maneuver the medical tool or device through passages.

FIG. 1 provides a side perspective view of a steerable medical device 10, according to one or more embodiments of the present subject matter. The steerable medical device 10 comprises a bendable body 12, a break-out unit 28 and an actuator 36. The bendable body 12 comprises at least two guide rings 14, housing at least two driving wires 16 and 16', a flexible backbone 18 for supporting the guide rings 14, as well as a fissure 40 for each one of the driving wires 16, intended to guide the driving wire 16. The guide rings 14 are hollow in the center and are fixed on the backbone 18 with an adhesive layer 42 by a designed interval. The assembly of the guide rings 14 in combination with the backbone 18 creates a channel 44 for accepting a secondary tool through the device 10. The bendable body 12 also defines a centroid Q as a center line of tube-like shape of the bendable body 12, with a proximal end C closer to the break-out unit 28, and a distal end D further away from the break-out unit 28. The backbone 18 may be mechanically fixed at the proximal end C and elastically steerable along the centroid Q.

Figure 2:
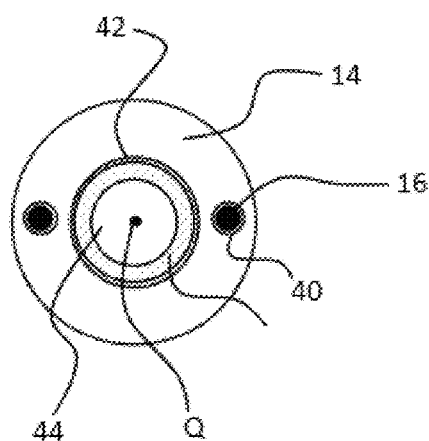
FIG. 2 is a front perspective view of a steerable medical device, according to one or more embodiments of the present subject matter.

FIG. 2 further provides a front cross sectional perspective view of a steerable medical device 10, provided in FIG. 1. Accordingly, the cross section view of the bendable body 12 at cross section A-A (See FIG. 1) more clearly details a guide ring 14 containing at least two guide fissures 40 for guiding the at least two driving wires 16. FIG. 2 further details the adhesive layer 42, the channel 44 for accepting a secondary tool, as well as further defining the centroid Q.

Returning to FIG. 1, the guide rings 14 may be fixed on the backbone 18 with the adhesive layer 42, and may hold the driving wires 16 and 16' in the respective fissures 40, while the driving wires 16 and 16' freely slide along the guide fissures 40. Between adjacent guide rings 14, the driving wire 16 and 16' stand without any mechanical support structures. The space between guide rings 14 allows for manipulation of one guide ring 14 with respect to a second guide ring 14, thus leading to steering of the medical device 10.

Figure 5:
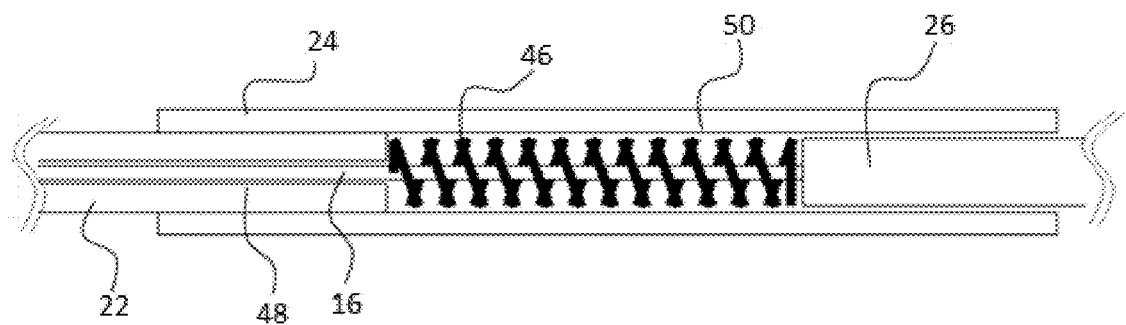
FIG. 5 details a side perspective view of at least a portion of a steerable medical device, according to one or more embodiments of the present subject matter.

The break-out unit 28 comprises a distal guide tube 22, a proximal guide tube 24, at least two break-out wires 26 and 26', and a spring 46 (See FIG. 5). The proximal guide tube 24 is mechanically fixed. Also, the distal guide tube 22 is fixed on the inner wall of the proximal guide tube 24. These distal and proximal guide tubes 22 and 24 create the proximal and the distal areas of eyelets, 50 and 48, respectively (See FIG. 5).

FIG. 1 further illustrates the actuator 36, which may be configured near the patient and is mechanically connected to the bendable body 12 via the break-out unit 28. The actuator 36 comprises a tractor 30 which is connected to the break-out wire 26, as well as a lead screw 32 and motor 34, for advancing and retracting the break-out wire 26 along the Q axis. The break-out wire 26 in this interval travels through free space and is kept straight.

Figure 3:
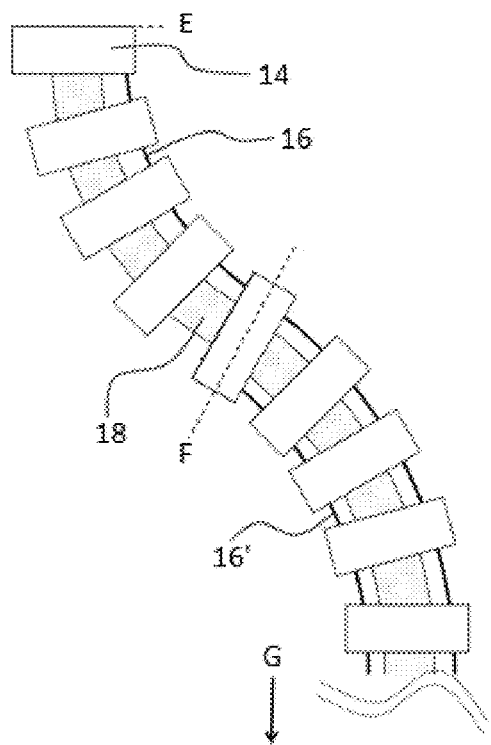
FIG. 3 provides a top perspective view of at least a portion of a steerable medical device, according to one or more embodiments of the present subject matter.
Figure 4:
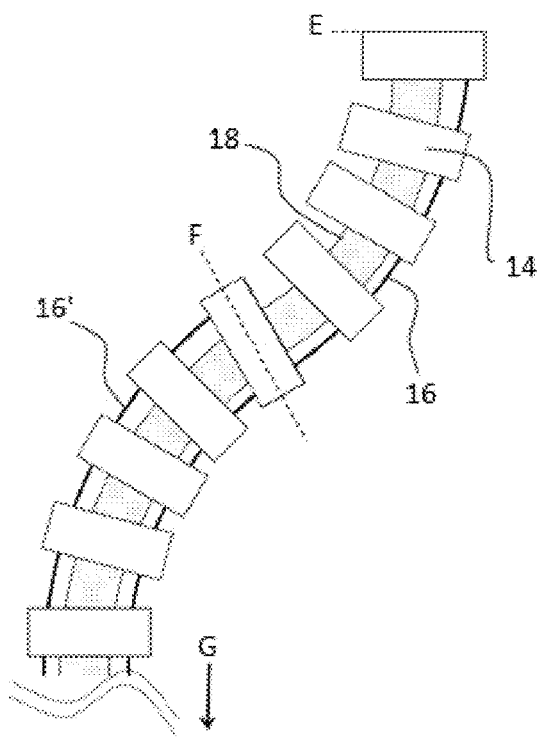
FIG. 4 provides a top perspective view of at least a portion of a steerable medical device, according to one or more embodiments of the present subject matter.

As depicted in FIGS. 3 and 4, the driving wires 16 and 16' are fixed to the guide rings 14 at different positions by fasteners 58. Specifically, the driving wire 16 is fixed to a first guide ring 14 at position E by a fastener 58, while the driving wire 16' is fixed to a second guide ring 14 at position F by a fastener 58'. The remainder of each driving wire 16 and 16' extent freely through the respective guide fissures 40 until they reach the break-out unit 28. The fasteners 58 and 58' may be attached to the respective guide rings by mechanical, chemical and/or sonic welding means. With these termination position E and F, the bendable body 12 is divided into two bending sections 100 and 100', which is a substantial bending area that comprise an assembly of the backbone 18, the driving wire 16 or 16' and the all guide rings 14 in this area. In FIGS. 3 and 4 we observe two different enactments of the subject steerable medical device 10, wherein FIG. 3 portrays a left arcing S bend, accomplished by first retracting the driving wire 16', followed by retracting the driving wire 16. The right arcing S bend in FIG. 4 is accomplished by first advancing the driving wire 16', followed by advancing the driving wire 16. Stated other ways, when the driving wire 16 is retracted by the motor 34, a bending section between position E and F bends to the direction of the driving wire 16 (FIG. 3). Also, when the driving wire 16 is advanced, the bending section between position E and F can bend to the opposite direction (FIG. 4). In the same way, when the driving wire 16' is retracted, a bending section between position F and G bends to the direction of the driving wire 16', and when advanced, the bending section bends to the opposite direction. At the bending section between position F and G, the bending moment from the driving wires 16 and 16' interfere with each other, but by choosing appropriate actuation forces for the driving wires 16 and 16', the bending section between position F and G can be bent independently. Consequently, by using two or more driving wires, two or more corresponding bending sections are independently bendable. As can be appreciated, additional bending sections may be added with additional driving wires and bendable bodies, which would result in additional independent bends.

As provided in FIG. 5, the proximal end of the driving wire 16 is connected to the break-out unit 28 by attaching the driving wire 16 to the break-out wire 26. The proximal area of the eyelet 50 includes the driving wire 16 and the break-out wire 26 and mechanically guides the break-out wire 26 along the Q axis. The proximal area of the eyelet 50 may include a spring 46, exemplified herein as a coil spring, for guiding the driving wire 16 along the Q axis. The spring 46 may touch the distal guide tube 22 and the break-out wire 26 at both ends. Between the distal guide tube 22 and the break-out wire 26, the spring 46 contracts when the driving wire 16 is extended by the break-out wire 26. While the spring 46 is compressing, the spring 46 acts to guide the driving wire 16 with a substantial identical inner diameter compared to the diameter before the spring 46 is compressed. Accordingly, retraction and advancement of the driving wire 16, via the break-out wire 26, is accomplished without buckling.

Moreover, the spring 46 stabilizes the motion of the break-out wire 26 and the driving wire 16 with the restoring force of the spring 46 from unpleasant mechanical motion caused by backlash in a moving component, for example the tractor 30 and the lead screw 32 in the actuator unit 36, when the break-out wire 26 is advanced.

As the break-out unit 28 incorporates one or more springs 46, the driving wire diameter may be decreased without inciting buckling. When transmitting actuation force from the actuator unit 36, the break-out unit with the spring 46 can avoid buckling of the driving wire 16, specifically in the bridging area from the bendable body 12 to the actuator unit 36. With the decreased diameter of the driving wire 16, an outer diameter of the bendable body 12 can be miniaturized while maximizing the size of the tool channel 44 in the bendable body 12. Therefore, the bendable body 12 can reduce invasiveness in treatments and can increase range of the tools being used. Furthermore, by converting the driving wire 16 to the break-out wire 26 with a larger diameter, the break-out unit 28 can increase tolerance of position alignment between the driving wire 16 and the motor 34 (or the handles) in the actuator unit 36. The break-out wire 26 can transmit retraction/advancement forces with a curvature that accommodates misalignment of direction of the forces from the motor 34 and the handles 52 to the driving wire 16. Therefore, the actuator unit 36 reduces costs for fabrication, assembly and maintenance and increases reliability of operation avoiding malfunctions caused by misalignment.

Also, by housing the driving wire 16 with the proximal guide tube 24 at the proximal end, the exposed area of the driving wire 16 can be reduced at the proximal end, and can be protected from damages induced by the external environment, for example mechanical collision, wearing, moisture, harsh chemical environments, and so on. Even partial damage in the driving wire 16 may potentially become the starting point for buckling of the driving wire 16 and/or disconnection of the driving wire 16.

Finally, as the break-out wire 26 has a thicker diameter than the driving wire 16, the break-out wire 26 can travel through longer free-spaces without buckling, to ultimately be connected to the actuators 36 (or the handles). Therefore, the actuators 36 (or the handles) connected to the break-out wire 26 can configure with a greater variety of layout options, especially with respect to the direction of the centroid. These layout options allow minimizing the actuator unit 36 size and increasing the number of the actuators connected to the driving wire 16.

Figure 6:
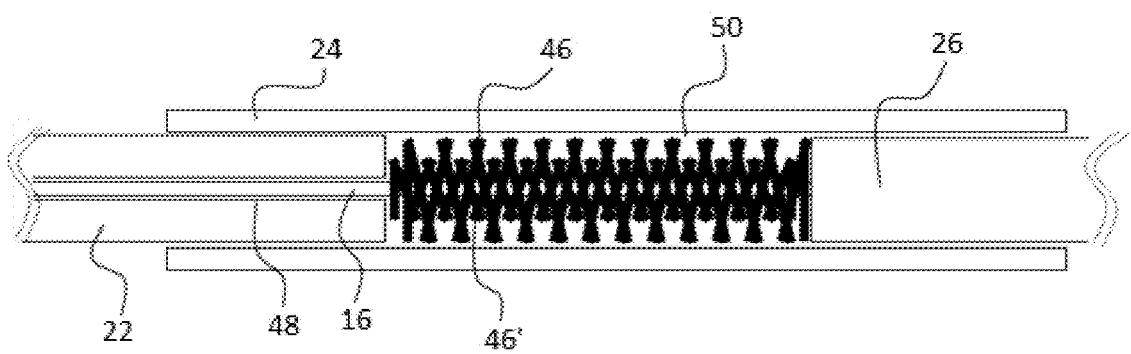
FIG. 6 illustrates a side perspective view of at least a portion of a steerable medical device, according to one or more embodiments of the present subject matter.

In various embodiments, multiple springs 46 may be utilized in conjunction with the subject steerable medical device 10. FIG. 6 depicts the use of a second spring 46' configured concentric to the first spring 46. These two springs 46 and 46' fill the proximal area of the eyelet 50 and mechanically guide the driving wire 16. The spring 46 and 46' are coil springs in this embodiment, and further have opposing spiral direction to each other, thus avoiding tangling of springs 46 and 46'. By having two or more than two springs 46 and 46', the spring can avoid reducing mechanical compliance as the diameter of the driving wire 16 is being miniaturized. Although coil springs have been depicted, it is contemplated that other resilient means, including leaf springs, tension elements, etc., may be substituted and/or augmented for one or both coil springs 46 and 46'.

By utilizing multiple coil springs 46, the driving wire 16 can be converted to the break-out wire 26 with the larger diameter keeping the appropriate stiffness of the springs 46. Therefore, the break-out unit 28 can be shortened along the centroid axis.

Also, the coil springs 46 can prevent buckling of the driving wire 12 with a smaller diameter since the effective inner diameter of the spring 46 against the driving wire 12 can be adjusted by adding coil springs 46 with smaller diameters to the inside of the existing spring(s) 46. Therefore, the break-out unit 28 can actuate a smaller bendable body and can reduce invasiveness in treatments increasing the range of surgical tools that may be used.

The motors 12 can be located serially along the Q axis by extending the break-out wire 26. Since the break-out unit 28 converts the diameter of the driving wires 16 and 16' to the diameter of the break-out wires 26 and 26', the appropriate diameter of the break-out wires 26 and 26' can be designed to extend the break-out wire 26 and 26' to the motors 12 without buckling of the break-out wires 26 and 26'. Therefore, the present disclosure can eliminate issues of buckling of the driving wires 16 and 16' from layout design of the motors 12 and allows actuating the bending body 12 miniaturized by the driving wires 16 and 16' with a much thinner diameter.

Figure 7:
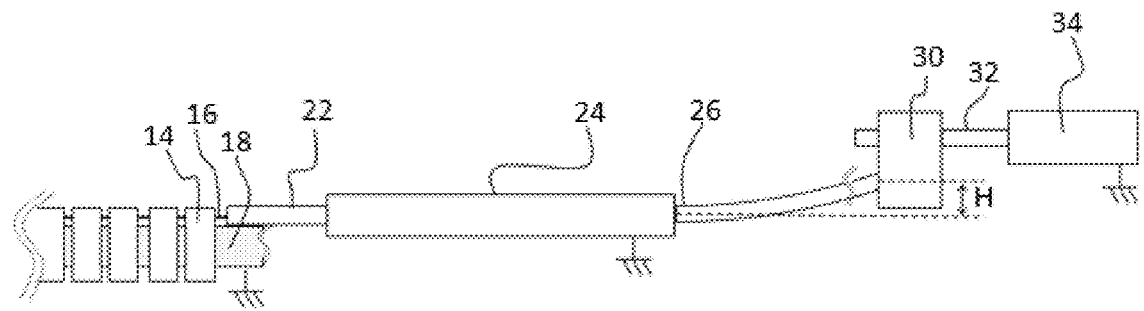
FIG. 7 depicts a side perspective view of a steerable medical device, according to one or more embodiments of the present subject matter.

Furthermore, the diameter of the break-out wire 26 can be selected to have enough robustness to eliminate any detriments associated with misalignment of the tractor 30 (FIG. 7). Misalignment (H) of the tractor 30 in FIG. 7 can be tolerated by deflecting the break-out wire 26 without buckling. Therefore, the present innovation can increase tolerance in the location of tractor 30 with respect to the proximal guide tube 24, and can allow reducing position calibration and countermeasures to misalignment by environmental factors, i.e. temperature, heat cycles and humidity.

Moreover, the steerable medical device's 10 robustness against misalignment allows a mechanical interface between the break-out wire 26 and the tractor 30, which allows the bendable body 12 to be exchanged, and the break-out unit 28 with the reusable actuator unit 36. The steerable medical device's 10 robustness against misalignment can accommodate position variability in the event of attachment, detachment and reattachment of various different individual parts, further expanding utility and advantages of the subject disclosure. Specifically, the steerable medical device can be developed as sterile disposable tools as well as limited time use tools after sterilization processes.

Figure 8:
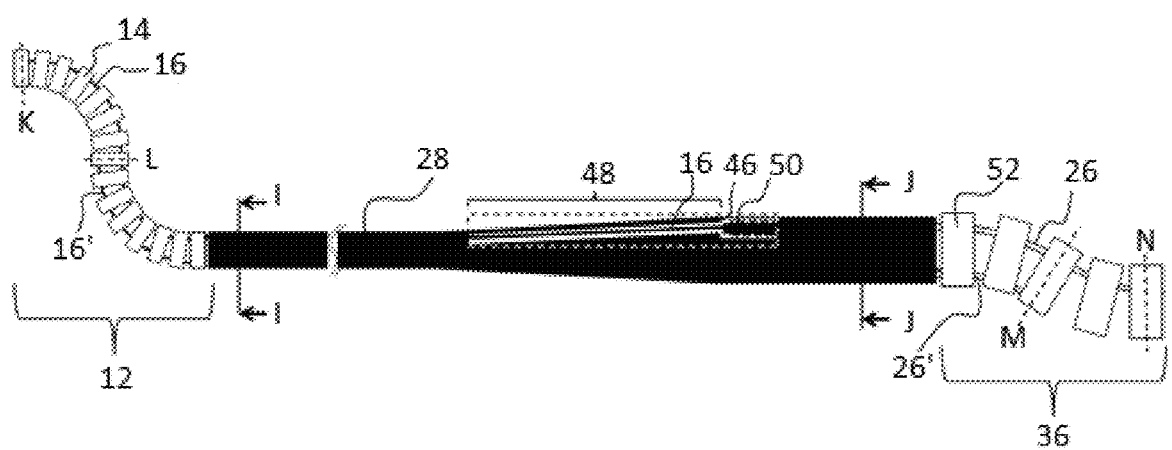
FIG. 8 depicts a side perspective view of a steerable medical device, according to one or more embodiments of the present subject matter.
Figures 9, 10:
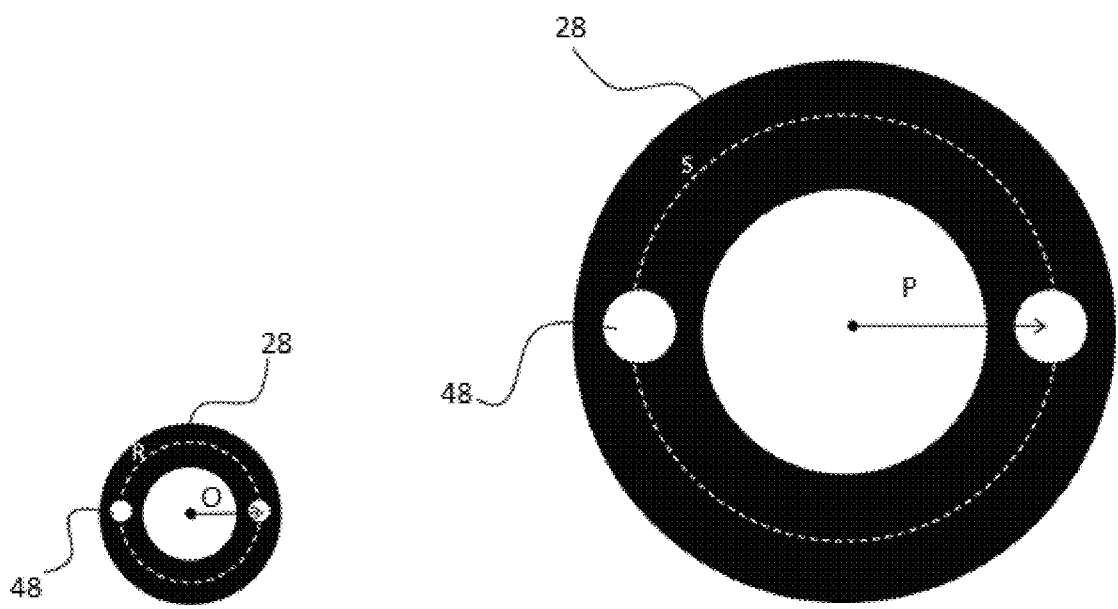
FIG. 9 provides a cross sectional view of at least a portion of a steerable medical device, according to one or more embodiments of the present subject matter.
FIG. 10 illustrates a cross sectional view of at least a portion of a steerable medical device, according to one or more embodiments of the present subject matter.

FIGS. 8 through 10 provide various views of a steerable medical device 10, employing a tapered break-out unit 28, and a manually operated actuator unit 36. FIG. 8 is the side view of the steerable medical device 10. FIGS. 9 and 10 are the cross-sectional views of the medical device 10 at line I-I and J-J. In this embodiment, the break-out unit 28 is tapered from a proximal side to a distal side. The distal end of the break-out unit 28 is increasing offset O of the driving wires 16 and 16', to offset P of the break-out wire 26 and 26'. At the same time, the circumference for circular layout of the break-out unit 28 also increases from the circumference R to the circumference S.

The actuator unit 36 includes rotating handles 52, which may be manipulated by an end user manually. The rotating handles 52 include handle eyelets (not shown in figure) and hold the break-out wires 26 and 26'. The break-out wires 26 and 26' can slide along the handle eyelets. Via the break-out wire 26, the driving wire 16 terminating at position K is connected to the rotating handle at position N. Also, via the break-out wire 26', the driving wire 16' terminating at position L is connected to the rotating handle at position M.

The rotating handles 52 are structurally similar to the bendable body 12. The rotating handles 52 are supported by an elastic tube (not shown in figure) and can bend just like the bendable body 12. In bending, each handle 52 can rotate the break-out wires 26 and 26'. Specifically, the rotating handle 52 at positions M and N determine the bending angle of the bendable body 12 at positions K and L, respectively. The rotating handles 52 can control bending angles of the multiple bending sections with the plural break-out wires by using the similar multiple bending sections.

More specifically, the control angle of rotating handles 52 may be configured to be smaller than the bending angle of the bendable body 12 since the offset R of the driving wire 16 and 16' are increased to the offset S of the break-out wires 26 and 26'. The ratio of the bending angle of the bendable body 12 to the control angle of the rotation handles 52 is proportionally inverse to the ratio of the offset R to the offset S. Furthermore, these proportions may be adjusted to allow for more or less finite control of the bendable body 12, thus further adding utility to the subject steerable medical device 10.

By devising a break-out unit 28 that increases the offset distance of the driving wire 16, the break-out unit 28 can make enough circular pitch for the break-out wire 26 when the circular pitch of the driving wire 16 in the bendable body 12 causes mechanical interference of the adjacent break-out wires 26, and can actuate the bendable body 12 with a smaller outer diameter. Accordingly, the bendable body 12 is capable of reducing invasiveness in use, and, due to the smaller diameter necessary for the bendable body 12, allows for an increase range of tools that can be inserted into the bendable body 12.

Furthermore, the ability to disconnect and connect the bendable body 12 to the break-out unit 29, allows for various parts of the steerable medical device 10 to be sterilization independently. Therefore, the bendable body 12 can be easily and economically sterilized without the need to sterilize the actuator unit 36 and/or break-out unit 28. Also, the bendable body 12 can be disposable while the actuator unit 36 and/or break-out unit 28 are reusable.

Moreover, the break-out unit 28 can be repeatedly connected in serial, which can further increase the circular pitch with multiple steps to reduce friction loss and risk of buckling in the fissure.

Also, in combination with the rotating handle 52 as an actuator unit, this increased offset distance reduces rotation angle of the rotating handle 52 to achieve a target bending angle of the bendable body 12. Therefore, users can achieve the target bending angle with smaller stroke of operation.

The rotating actuation handle 52 allows an operator to actuate the bendable body 12 manually by using the rotational motion on the plane corresponding to the bending plane of the bendable body 12, the handles 52 can actuate the multiple driving wires 16 with simple and small structure. When the bendable body 12, employing the multiple driving wires 16, creates multiple sections bending along the centroid, the handles 52 can configure tandem elements with independent rotational motions to control multiple sections bending individually. Also, when the bendable body 12 with the multiple driving wires 16 includes multiple degrees of bending in one bending section, the handle 52 can configure an element with multiple rotational motions. Therefore, the actuator unit 36 can be miniaturized allowing the steerable medical device 10 to be mobile and easy to configure and operate in any desired local.

The rotating actuation handle 52 can be connected to the actuators with the ability to disconnect and connect the entire structure between the bendable body 12 and the rotating actuation handle 52 from the actuators. In this implementation, both the driving wire 16 and the break-out wire 26 can be capsuled and can be protected from the damage induced by the external environment, for example mechanical collision, wearing, moisture, harsh chemicals, and so on.

Figure 11:
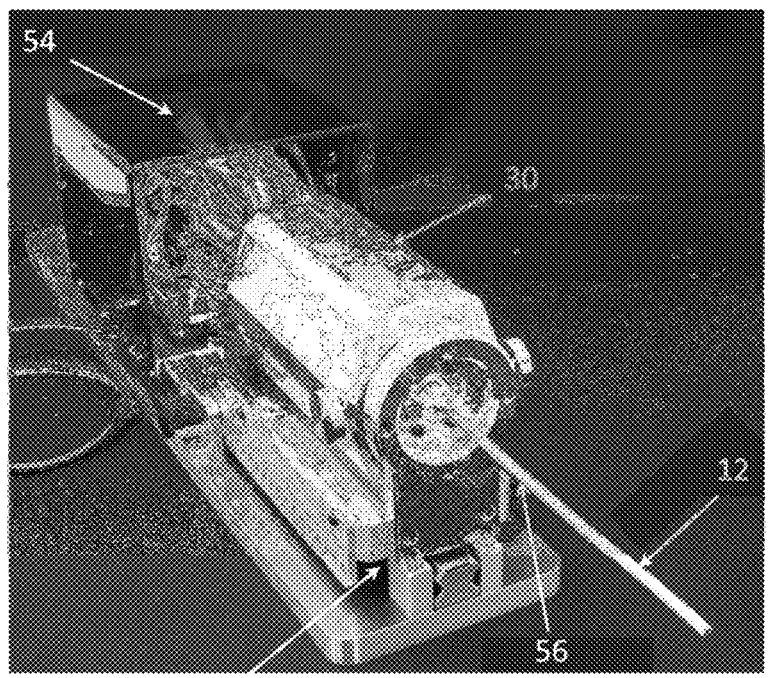
FIG. 11 provides a photograph of an exemplary steerable medical device, according to one or more embodiments of the present subject matter.
Figure 12:
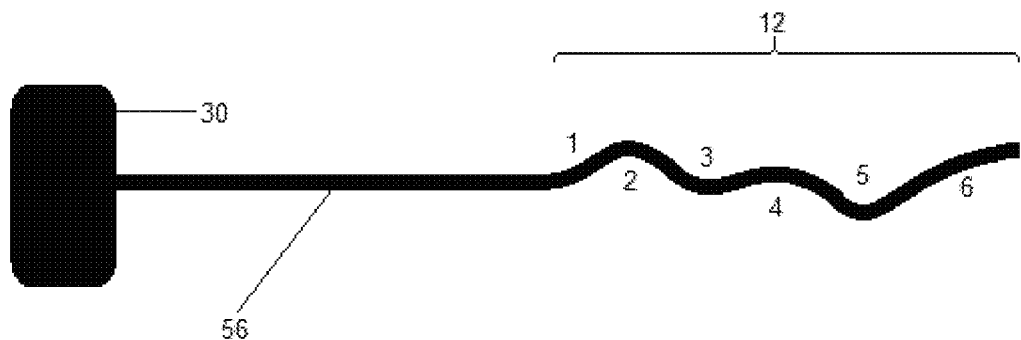
FIG. 12 is a photograph providing at least a portion of an exemplary steerable medical device, according to one or more embodiments of the present subject matter.

The embodiment of the present disclosure provided as photographs in FIGS. 11 and 12, have a similar configuration of the steerable medical device in FIGS. 1 and 2, however, the bending body 12 includes six bending sections. FIG. 11 is the perspective view of the steerable medical device 10, and FIG. 12 is top view of the bendable body 12 with the six bending sections enacted. The steerable medical device 10 in the present embodiment comprises a motor circuit 54 comprising multiple motors 34, a tractor 30, an intermediate shaft 56 and a bendable body 12. An intermediate shaft 56 corresponds with the break-out unit 28. The actuator unit 36 corresponds with the motor circuit 54 and the tractor 30. The six bendable sections are accomplished by six sets of driving wires and guide rings attached to the driving wires at staggered locations. In addition, actuators would be required for each of the six driving wires to facilitate independent bending of the medical device 10 by retraction or advancement of each driving wire.

Figure 13:
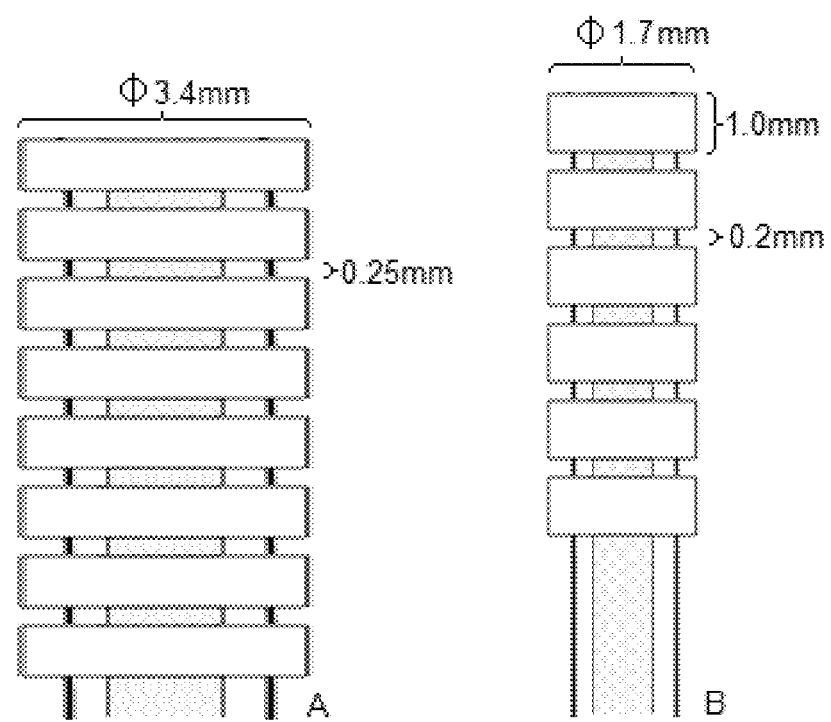
FIG. 13 is a photograph providing at least a portion of an exemplary steerable medical device, according to one or more embodiments of the present subject matter.

FIG. 13 provides a photograph of exemplary bendable bodies 12 according to one or more embodiments of the present subject matter. The bendable bodies 12 provided in FIG. 13 were provided in two sizes. The one example ("A") has an outer diameter of 3.4 mm and guide rings having a pitch of 0.25 mm. Example A also includes a tool channel 44 with the diameter of 1.4 mm. The second example ("B") has an outer diameter of 1.7 mm and the guide rings with pitch of 0.2 mm. Both examples have a backbone made of super-elastic titanium-nickel alloy. The backbones were machined by laser cutting and include integrated bending flexures at the position between adjacent guide rings so that the bendable body 12 can bend on the bending plane.

By incorporating multiple bending sections, the steerable medical device 10 can control the position of the tip of the bendable body 12 with a deeper reachable area and with wide orientation options. Also, the bendable body 12 can reach the target through complicated pathways by using multiple curvatures in the body 12.

Figure 14:
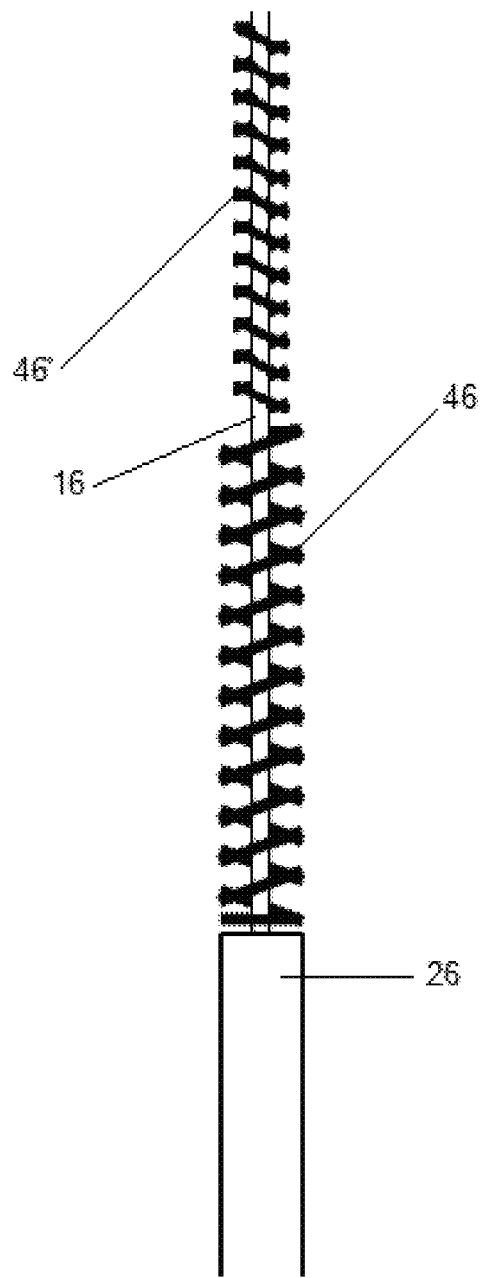
FIG. 14 is a photograph providing at least a portion of an exemplary steerable medical device, according to one or more embodiments of the present subject matter.

FIG. 14 shows a closed-up view of the connection of the driving wire 16 with the break-out wire 26. Here, driving wires 16 with a diameter of 0.12 mm were connected to the break-out wires 26 with the diameter of 0.35 mm. The driving wire 16 was inserted into the break-out wire 26 and was fixed with an adhesive. Two coil springs 46 and 46' are located around the driving wire and prevent buckling of the driving wire 16. In the image provided in FIG. 14, the outer spring 46 and inner springs 46' have been partially separated to better illustrate their relationship with one another and the bendable body 12. The spiral directions of the springs 46 and 46' can be seen to be clockwise and counter-clockwise, respectively. The driving wire 16 with the diameter of 0.12 mm at 100-mm length has been shown to transmit target pushing force (>5 N) by using this exemplary steerable medical device 10.

The invention claimed is:

1. A medical apparatus comprising:
    a bendable body having at least a first driving wire configured in the bendable body;
    an expansion unit comprising:
        a first break-out wire attached to the first driving wire; and
        a contracting guide substantially surrounding the first driving wire along at least a portion of a longitudinal direction of the first driving wire, the contracting guide being movable with respect to the first driving wire; and
    an actuator configured to retract and advance the first driving wire via the first break-out wire and configured to maneuver the bendable body;
    a tapered break-out unit housing the first break-out wire and first driving wire;
    wherein, the contracting guide is movable along the longitudinal direction of the first driving wire, and
    wherein first break-out wire has a larger diameter than the first driving wire.

2. The apparatus of claim 1, wherein the bendable body has a channel about the center of the bendable body, and wherein a diameter of the channel is substantially the same before, during, and after the bendable body is maneuvered.

3. The apparatus of claim 2, wherein the channel is configured to receive various surgical tools selected from the group consisting of a biopsy tool, an endoscope, a cutting tool, a slicing tool, a light, derivatives thereof, and combinations therefrom.

4. The apparatus of claim 1, wherein the first driving wire extends to a distal end of the bendable body and is offset from a center line of the bendable body.

5. The apparatus of claim 1 wherein the break out unit comprises a guide tube to guide the break-out wire.

6. The apparatus of claim 1, wherein the contracting guide comprises a first spring parallel to and surrounding the first driving wire.

7. The apparatus of claim 6, further comprising a second spring configured about the first spring and having a spiral direction different than that of the first spring.

8. The apparatus of claim 1, further comprising a second driving wire configured in the bendable body, and a second break-out wire attached to the second driving wire and a second contracting guide substantially surrounding the second driving wire, wherein the second break-out wire is in communication with the actuator.

9. The apparatus of claim 8, wherein the second driving wire partially extends into the bendable body and is offset from a center line of the bendable body.

10. The apparatus of claim 8, wherein the actuator is configured to retract and advance the second driving wire via the second break-out wire.

11. The apparatus of claim 8, wherein the second driving wire is configured in a different position than the first driving wire, with respect to the bendable body.

12. The apparatus of claim 8, further comprising at least a third spring parallel to and surrounding the second driving wire.

13. The apparatus of claim 8, wherein a diameter of the second break-out wire is greater than a diameter of the second driving wire.

14. The apparatus of claim 8, further comprising a third driving wire configured in the bendable body, and a third break-out wire attached to the third driving wire, and a third contracting guide substantially surrounding the third driving wire, wherein the third break-out wire is in communication with the actuator.

15. The apparatus of claim 1, wherein a diameter of the first break-out wire is greater than a diameter of the first driving wire, and the first break-out wire is configured to push the contracting guide when the contracting guide contracts.

16. The apparatus of claim 1, wherein the bendable body comprises:
at least two guide rings, wherein the at least two guide rings are aligned parallel to one another and have a distance between them, and each guide rings comprises at least one fissure configured to at least accept the first driving wire or a second driving wire.

17. The apparatus of claim 16, further comprising a first spring parallel to and surrounding the first driving wire and a second spring configured about the first spring and having a spiral direction different than that of the first spring.

18. The apparatus of claim 1, wherein the break-out unit is configured to increase the offset distance of the driving wire proximal to the actuator of the apparatus.

19. The apparatus of claim 1, wherein the actuator comprises an actuation handle in communication with the first break-out wire, such that manipulation of the actuation handle corresponds to a bending of the bendable body.

20. The apparatus of claim 1, wherein the break-out unit is configured to be detachable from an actuator.

* * * * *